United States Patent [19]

Clawson et al.

[11] 4,430,994

[45] Feb. 14, 1984

[54] RESPIRATORY GAS HEATING AND HUMIDIFYING METHODS AND APPARATUS

[76] Inventors: Burrell E. Clawson, 823 W. 16th, Newport Beach, Calif. 92663; James Weigl, 2241 Chicago Ave., Riverside, Calif. 92507

[21] Appl. No.: 262,080

[22] Filed: May 11, 1981

[51] Int. Cl.³ .................................................. A61M 15/00
[52] U.S. Cl. ........................ 128/203.27; 128/204.13; 128/204.14; 128/205.12; 55/257 NP; 55/462; 261/112; 261/153
[58] Field of Search .............. 128/203.16, 200.11, 128/203.17, 200.13, 203.26, 206.22, 203.27, 204.13, 1 B, 204.17, 200.21; 261/153, 154, 130, 142, 103, 106, DIG. 65, 112; 55/DIG. 35, 319, 355, 280, 461

[56] References Cited

U.S. PATENT DOCUMENTS

| | | | |
|---|---|---|---|
| 1,970,234 | 8/1934 | Huff | 261/153 |
| 2,416,885 | 3/1947 | Skilbeck | 261/154 |
| 2,633,842 | 4/1953 | Higgs | 261/153 |
| 3,231,490 | 1/1966 | Fry | 261/112 |
| 3,509,967 | 5/1970 | Ballard | 55/319 |
| 3,853,516 | 12/1974 | Lyshkow | 55/319 |
| 3,954,920 | 5/1976 | Health | 128/203.27 |
| 4,110,419 | 8/1978 | Miller | 128/204.13 |
| 4,146,026 | 3/1979 | Montalvo | 128/200.13 |
| 4,327,718 | 5/1982 | Cronenberg | 128/205.12 |
| 4,333,451 | 6/1982 | Paluch | 128/205.12 |

FOREIGN PATENT DOCUMENTS

| 2263720 | 7/1973 | Fed. Rep. of Germany | 128/203.26 |
|---|---|---|---|
| 627820 | 8/1978 | U.S.S.R. | 128/206.22 |

Primary Examiner—Lee S. Cohen
Assistant Examiner—Christine A. Fukushima
Attorney, Agent, or Firm—Grover A. Frater

[57] ABSTRACT

Respiratory gas is delivered to a patient enclosure past a variably heated surface over which a film of water migrates and whose wetness is visible through a transparent cover which is recessed at the water film side to define water inlet, gas flow, and excess water removal paths.

16 Claims, 12 Drawing Figures

RESPIRATORY GAS HEATING AND HUMIDIFYING METHODS AND APPARATUS

TECHNICAL FIELD

This invention relates to methods and means for heating, humidifying and delivering respiratory gas to a patient.

BACKGROUND ART

The respiratory gas that is delivered to persons who are ill usually is a mixture of air and oxygen and, in most cases, it is desirable to provide the gas to the patient at a temperature nearly equal to body temperature. Because body temperature almost always exceeds the temperature of the ambient atmosphere, the respiratory gas is heated.

It is required that respiratory gas be humidified. A positive means for adding humidity is required because both the air and oxygen are usually supplied from very dry sources of compressed air and compressed oxygen. Further, it is preferred that the humidity level be near 100 percent in most cases. That preference, combined with the requirement for a positive means for accomplishing humidification, has led to the near universal practice of humidifying respiratory gas by bubbling it through or passing it over heated water. Sometimes the gas is heated and it vaporizes the water. Whichever scheme is employed, the humidification is accomplished by bubbling gas through or passing it over water.

That scheme is simple and reasonably effective but it creates very serious practical problems. Unless the bubble path is very long, adequate humidification requires high temperature. If something goes amiss, the patient may receive very hot respiratory gas. In the case of an infant in an incubator or other enclosed environment, that is not easily detected and could be disastrous. Further, the pressure versus time plot of respiratory gas, as delivered to the infant, can very with water level in the humidifier. Low water level often results in higher gas temperature to the infant in some present designs. In addition, that old method presented a continuing nuisance problem to the nurses and others who attend infants being supplied with respiratory gas. Since the gas is supplied continuously at far higher volume than needed by the infant, and since it is humid and warmer than ambient atmosphere, condensation in large amounts occurs within the flow line. If the lines are arranged so that it is "all downhill" from humidifier to patient, the patient receives much condensate along with the respiratory gas. If it is not "all downhill," the condensate collects at the low point in the tubing. If the line is not drained periodically, condensate can disrupt the desired pressure of respiratory gas to the patient, and eventually be blown en masse up or down to the patient.

DISCLOSURE OF INVENTION

The invention makes use of a novel humidifying element which is itself inventive. Water is made to flow, as a film, over a heat transfer element. Flow is slow, preceeding, in the preferred embodiment, as a slow migration so that the film is heated to a temperature approaching that of the element. The respiratory gas is flowed over the water film and becomes more humid as it proceeds. As humidity increases during the course of flow, increased temperature is required to accomplish further humidification. Thus it is that gas temperature is increased as humidity is increased.

In preferred form the flow path over the heat transfer element and its water film constitutes a labyrinth in which humidity level is controlled by controlling the supply of water for the film. The supply is controlled to control the portion of the labyrinth over which the water film extends. Gas temperature is controlled by controlling the temperature of the heat transfer element.

In preferred form the humidifying element is arranged for mounting and operation within the enclosure if the patient is being maintained in an enclosure. If the atmosphere within the enclosure is controlled, the system approaches or becomes isothermal. The heating element itself is included in the enclosure. However, the invention is not limited to that arrangement. If preferred by the user, whether or not the patient is in a controlled environment, the humidifier and its heater may be positioned outside that environment. Thus, for example, they may be mounted on an "IV" pole. That is entirely feasible. Visual means and a control are provided for controlling humidification. In the method of the invention, condensation can be prevented. Prevention is not mandatory, however, because the invention provides an improved water trap.

To provide the advantages described above, and those that become apparent below, is an object of the invention. Thus, it is an object to provide an improved humidifier, an improved heater-humidifier combination, an improved subsystem of heater-humidifier-heat controller and water supply control, an improved water trap when desirable, and an improved method not only for accomplishing humidification and its control but for conducting the humidification process both when the patient is contained in a controlled environmental enclosure and when he is not.

DESCRIPTION OF PREFERRED EMBODIMENTS

The invention is applicable to the heating and humidifying of respiratory gas whether that gas is to be supplied to an adult, child, or newborn infant, and whether the gas is to be delivered to a point within a controlled environment or not. The most difficult and demanding application is the treatment of respiratory gas to be supplied to an infant in a controlled environment, as in an incubator. Because of that difficulty, and becasue the method and apparatus of the invention are especially useful in that application, the embodiments selected for illustration, and which are now considered to be the best mode of practicing the invention, relate to the heating and humidification of gas to be furnished in that application.

Figure 1:
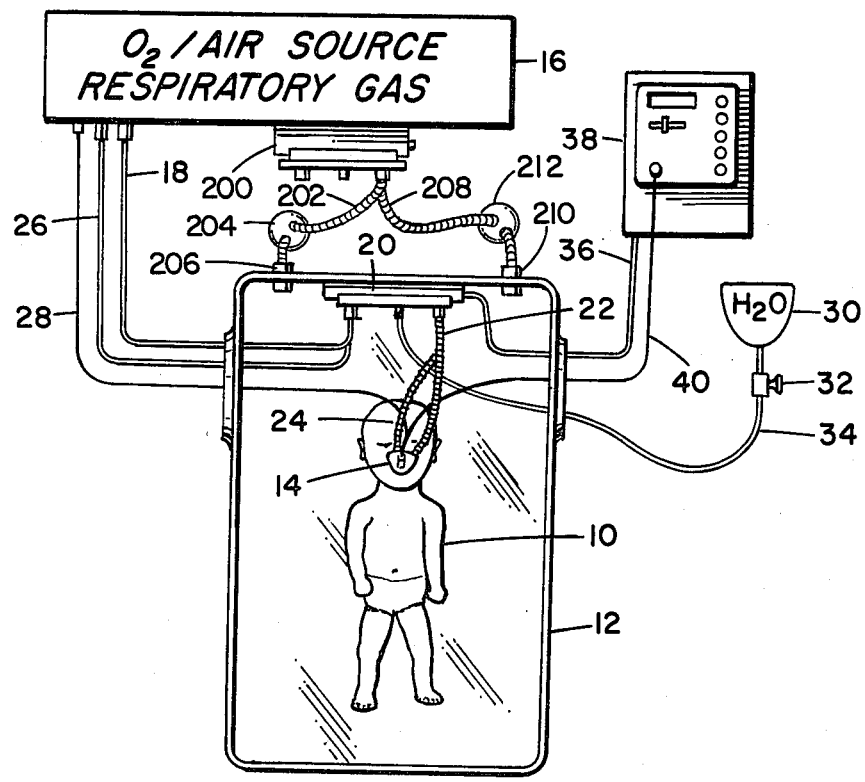
FIG. 1 is a schematic drawing illustrating how the apparatus of the invention is used in practicing the preferred method of the invention.

In FIG. 1, an infant 10 is shown in an enclosure 12, an incubator, in which temperature is controlled. Respiratory gas is supplied to the infant using a manifold 14 which is connected to the infant at its mouth or through an intubation set. The manifold is used to deliver fresh respiratory gas and to receive exhaled gas.

The respiratory gas is a mixture of air and oxygen, and it is supplied from a source 16. The gas is delivered to the infant by a flow line 18 which extends from the source 16 through a humidifying unit generally designated 20. Gas is delivered to the manifold 14 from the humidifying unit 20 by another flow line 22. Exhaled gas is directed by the manifold 14 to an exhaust line 24 which extends from manifold 14 to another connection at the humidifying structure 20. From that structure exhaust gas and unused gas is returned to the source 16 by a return line 26.

The source in this case is a respirator, and it samples the pressure in the system at the manifold 14. The pressure is communicated to the respirator 16 and its control elements by a line 28.

Water, which is evaporated into the respirator gas at the humidifier 20, is supplied to that unit from a water container 30 through a flow control valve 32 and a flow conduit 34. The humidifying structure includes a heater, power for which is supplied by a heater core 36 from a controller 38. That controller has as its purpose controlling the amount of energy supplied to the heater as a function of the temperature of respiratory gas being supplied to the infant at the manifold 14. To that end, a heat sensor is provided at the manifold, and its output signals are supplied to the controller 38 by a sensor line 40.

The controller 38 is provided with an adjusting element which permits selection of the temperature at which gas is to be furnished to the infant. An amount of energy is supplied to the heater portion of the humidifier to maintain the selected temperature at the manifold. While not visible in FIG. 1, the humidifying structure includes a means for indicating visually, on a relative basis, the extent to which the water is made available for humidification of the respiratory gas. The amount of water that is supplied to the humidifier is controlled by adjustment of the valve 32. Ordinarily, both the controller 38 and the water bottle 30 are mounted on an IV pole standing adjacent the incubator 12. Water is supplied to the humidifier by gravity and, ordinarily, there is no need for removal of excess water. The humidifier is arranged so that any excess water that must be removed is removed in the gas flow return circuit.

It is a feature of the invention, when the point of respirator gas delivery is within an enclosure, to mount the humidifying apparatus within the enclosure. When it is controlled, the temperature in the enclosure will approach the temperature at which respiratory gas is supplied to the patient, in which case an isothermal condition is achieved. The humidifying unit includes both a humidifier and a heater. The heater has an effect upon the temperature within the enclosure, but, in all but the abnormal case, the effect is simply to require less input to the incubator to maintain a selected internal temperature. Thus it is that the isothermal condition is not upset by inclusion of the heater within the enclosure. It is permissible, within the invention, to mount the heater at the outside of the enclosure, provided that there is a thermal connection between that heater and the humidifying element inside the enclosure.

Figures 2, 3:
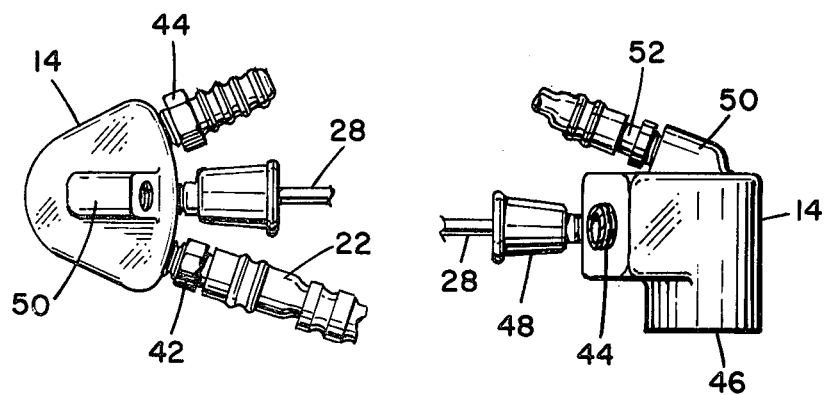
FIG. 2 is a top view of the respiratory gas manifold of FIG. 1 together with fragments of a hose and a sensor.
FIG. 3 is a view in side elevation of the respiratory gas manifold with fragments of sensors mounted thereon.

The coupler unit is shown in FIGS. 2 and 3. It is provided with an inlet 42 at which respiratory gas is supplied to the unit. It has an outlet 44 to which the return line 24 is connected. At its lower side 46, visible in FIG. 3, it is provided with an opening by which gas is supplied to the patient and by which exhaust gases are returned to the outlet 44 which is shown in cross-section in FIG. 3. The element 48 is a pressure sensor. It senses pressure within the manifold 14 and communicates that pressure via the tube 28 to the respirator 16.

At the upper side of the unit 14 is a projection 50 which is formed with a through opening into which a temperature sensor is inserted. The temperature sensor is visible in FIG. 3 where it has been identified with the numeral 52.

Figure 4:
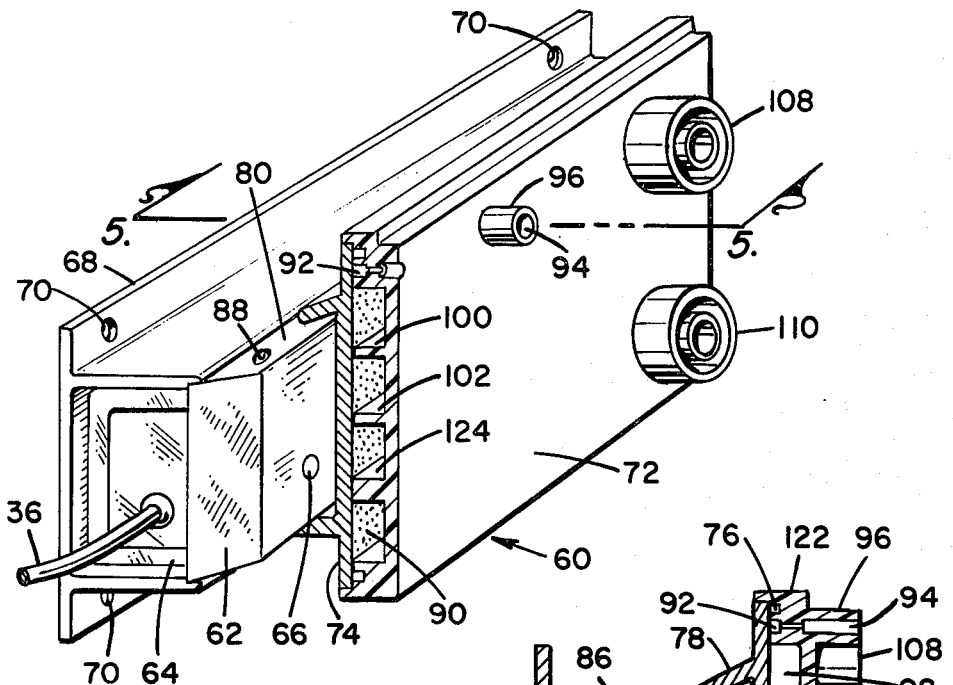
FIG. 4 is an isometric view of a heater-humidifier-heat transfer member assembly in which the humidifier is shown in cross-section.

The humidifier assembly is shown in assembled condition in FIG. 4. The humidifier 60 clamps onto a heat transfer element 62 which is in thermal communication with an electric heater 64 by being bolted to the enclosure. The bolts are not visible, but one of the openings through which the bolts extend is visible and it is numbered 66. Those three elements are mounted on a channel-shaped bracket 68 which has outwardly extending flanges at the closed end of the channel. Those flanges are provided with mounting holes by which the whole unit may be mounted within an enclosure such as an incubator or other enclosure for a patient. For identification, the mounting holes have been numbered 70. A portion of the power cord 36 is visible in FIG. 4. It extends from the open end of the channel-shaped bracket and through the side opening of the incubator (see FIG. 1) to the controller 38. A combination of the bracket 68, the heater 64, and the heat exchange structure 62 are permanently interconnected as part of the assembly. The humidifier element 60, however, is arranged so that it can be attached and removed from the heat exchange element 62 with relative ease. The manner of their interconnection is best illustrated in FIG. 5.

Figure 5:
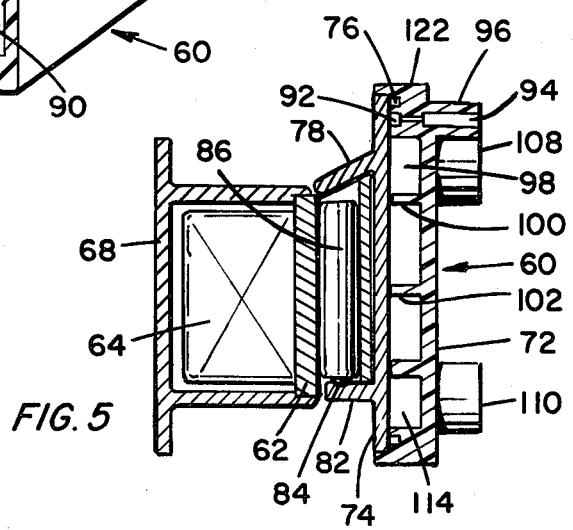
FIG. 5 is a cross-sectional view taken on line 5—5 of FIG. 4.

Turning to FIG. 5, in this embodiment the humidifier is formed by only three parts—a cover plate 72, a heat transfer plate 74, and a sealing member 76 which is disposed in a groove that extends entirely around the inner face of the front plate near its periphery. The arrangement of the seal is better seen in FIG. 6.

In FIG. 5 the heat transfer plate 74 is generally a flat plate, rectangular in shape as indicated in FIG. 4, and it is formed with two rearward extensions. One of those extensions is numbered 78. It extends rearwardly from the plate and downwardly at the same angle which the upward surface of the heat transfer member 62 is formed. The lower face of the heat transfer element 62 is formed at a similar angle so that the upper and lower surfaces lie in parallel planes. However, the rearward extension 82 at the lower side of the heat transfer plate 74 extends straight back. At its outer end it is formed with an upwardly extending lip, and that lip is arranged so that it engages the ball 84 of a spring-biased ball detent structure 86. While other constructions may be employed, in this case the ball detent is a standard unit formed by a cylindrical case which contains a compression spring and a ball. The spring and the ball are trapped within the case because the ends of the case are partially closed. The spring is compressed so that the ball detent 84 is made to extend, in part, from the housing. The ball engages the lip on the upper side of the lower extension 82 to retain the lower end in place. Because the upper "hanger" extension 78 slopes downwardly, the humidifying element 60 is clamped firmly with its heat transfer plate 74 in thermal communication with the heat transfer member 62. There are only two ball detents 86, and they are mounted in openings that are bored through the heat transfer member 62. One of those openings, 88, is visible in FIG. 4. The end result is that the humidifying element may be fastened or removed from the remainder of the assembly with a simple snap action, and when assembled, a good thermal contact from the heater 64 to the heat transfer plate 74 is accomplished.

In FIG. 4 the forward face 90 of the heat transfer plate 74 has been stippled to indicate that the surface has a special characteristic. In this preferred embodiment the heat transfer plate is made of aluminum material on whose forward face a thin coating of thin water film creating material has been attached or bonded. In this case the film creating material is a ceramic. The ceramic coating is preferred, but other coatings, and even mere roughing of the forward surface, can accomplish the required result. It will be shown later that water is supplied to the upper region of the plate. That water is to flow or migrate downwardly over the surface of the plate, wetting it to form a very thin layer on the surface. The water is required to form a thin film that will be heated by the heat transfer plate 74 so that the heat will be conducted to the exposed face of the water film where it accelerates evaporation of the water to the respiratory gas which flows over the film.

Figure 6:
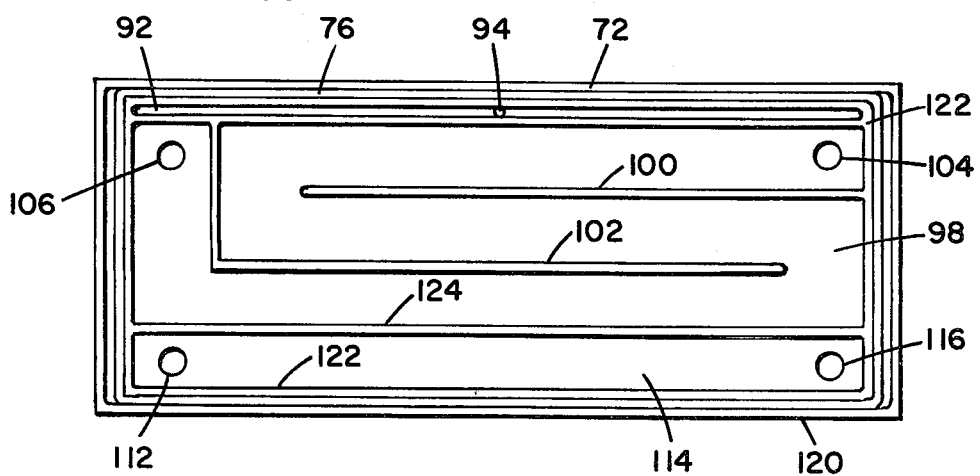
FIG. 6 is a view in rear elevation of the transparent cover plate of the humidifier.
Figure 7:
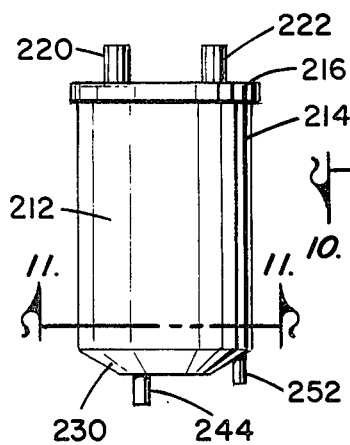
FIG. 7 is a view in side elevation of the special condensation trap.
Figure 8:
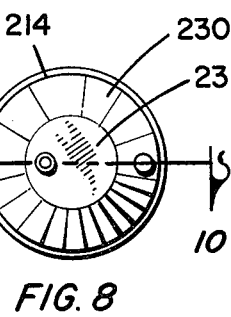
FIGS. 8 and 9 are bottom and top views, respectively, of the trap.
Figure 9:
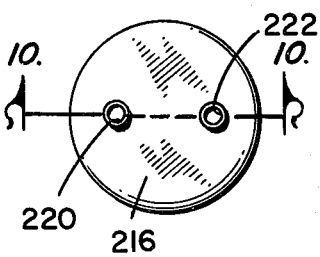

The cover plate 72 has portions of its rearward face recessed in three separate regions. When the cover plate is assembled with the heat transfer plate, the portions of the cover plate that are not recessed serve to separate the forward heat transfer surface of the heat transfer plate into three separate areas. The upper elongated groove 92 is a water distribution groove which is filled with water via a water inlet metering opening 94 which extends through the front plate and a coupling boss 96 to open to the forward face of the front plate 72. That recess 92 is separated from the recess 98 which is formed into a labyrinth by ribs 100 and 102. Those ribs are simply formed by the rear surface of the front plate which has not been recessed away. A labyrinth is formed which extends from an inlet opening 104 which affords communication between the labyrinth and the exterior of the humidifier at its forward face. At the other side, in FIG. 6, the left side, the outlet opening 106 affords communication from the labyrinth to the forward side of the front plate. At the forward side, the plate is formed with concentric forwardly extending coupling elements. The coupling element associated with opening 106 is visible in FIGS. 4 and 5 where it is numbered 108. The other coupling element 110 that is visible in those two figures is the coupler that is associated with outlet opening 112 in FIG. 6. That opening affords communication between the third or lower region 114 of the front plate to the forward side of the front plate. The other opening, the one at the lower right in FIG. 6, is numbered 116 and it affords communication from the region 114 to the forward face of the humidifier unit. The coupling elements associated with openings 114 and 116 are not visible in the drawings. However, those couplers are like the couplers 108 and 110 that are shown in FIGS. 4 and 5.

Since most of the rear face of the forward plate has been recessed away, it is appropriate to identify those portions that remain. At the very outer edge around the entire periphery, the rear plate is formed with a lip 120. The heat transfer plate 74 is shaped to fit exactly within that rim, and the rim is used, in combination with an adhesive, to fasten the heat transfer plate and the front plate together. Inside that rim is a peripheral region 122 which serves to define the outer limits of the second region 98 and the third region 114 of the front plate rear face. It is in the upper side of that margin in which the water supply groove 92 is formed. Because the groove is not interconnected with the next recessed region 98, there is no communication between the water groove 92 and the labyrinth section 98 except as will be explained below. The labyrinth region 98 and the region 114 are separated by a separater rib 124. That rib is continuous and precludes communication between the labyrinth 98 and the recess 114 except as hereinafter explained. The other feature that is visible in FIG. 6 is the sealing member 76 which is disposed in and occupies the whole of the groove around the outer periphery of the rear face just inside the outer lip 120.

As best shown in FIGS. 4 and 5, the heat transfer plate 74 and the front plate 72 are assembled so that the marginal portions 122 of the rear face of the front plate and the ribs 100 and 102 in the divider 124 engage the forward surface, the heat transfer surface, of the heat transfer plate 74. Respiratory gas entering at opening 104 in FIG. 6 is free to travel in the recess 98 between the marginal area 122 and the rib 100, and then in the space between the ribs 100 and 102, and finally in the space between the rib 102 and the divider 124 to exit at the opening 106. Spent gas entering opening 112 is free to flow between the peripheral wall 122 and the divider 124 to the outlet opening 116. The separator 124 and the marginal portions 122 are affected to keep those two flow paths separate so that flow in one is excluded from the other. However, the forward face 90 of the heat transfer member 74 is coated with ceramic, or otherwise treated or coated, so that its surface is sufficiently irregular to permit water to migrate down the surface 90 past the separator walls 100 and 102 and the divider 124. Thus, if water is introduced at the water inlet coupler 96, so that it flows through the metering opening 94 to the water distribution groove 92, that water will flow, or proceed by wetting action, or migrate down the plate so that a film of water will be formed on the inner surface 90 of the transfer plate. The exposed surface of the resulting water film is heated. That heating is efficient because only a thin film is formed. The water evaporates and is added to the gas that flows through the labyrinth and to the discharge passage 114.

The supply line 18 of FIG. 1 is connected to inlet opening 104 in FIG. 6. Fresh gas from the supply line flows through the labyrinth and out the opening 106 to which the supply line 22 is connected. The return line 24 from the manifold 14 is connected to the humidifier at opening 112. That exhaust gas flows along the third or lower region of the humidifier and out the opening 116 to be returned by line 26 to the respirator 16.

Whether the humidifying assembly be mounted within the patient's enclosure or on an IV pole, it is oriented so that the humidifier plates lie in a substantially vertical plane, so that the upper and lower sides of the unit are substantially horizontal and so that the water inlet fitting 96 is toward the upper side. Thus, it is mounted and oriented in the fashion indicated in the several drawings. As a consequence of that arrangement, the water inlet groove 92 lies above the labyrinth flow region and the return or exhaust region of the heat transfer plate. Enough of the front plate is transparent to permit viewing, through the plate, of the heat transfer surface 90. In this embodiment, the whole of the front plate is transparent. In this preferred form the front surface of the heat transfer plate 74 changes color. More properly, it changes it shade when it is wet. Thus, it is a simple matter to determine from the exterior of the humidifier what portion, if any, of the heat transfer surface 90 is wetted. The water flow control valve 32 of FIG. 1 is turned so that a selected portion of the transfer or evaporation plate is wetted. By that means the degree of humidification can be controlled, something that was generally not possible in the prior method. If the entire plate is wetted and there is excess flow, that flow will proceed by gravity to the third or exhaust region of the humidifier to be carried away in the return line 26 back to the respirator 16.

It is one of the advantages of the invention that the humidifier can be sterilized in a gas sterilizer. However, it will be apparent from the several figures of the drawings that this is an apparatus that can be produced very inexpensively and can, in fact, be considered to be disposable.

Returning to FIG. 1, there is a second humidifier 200 mounted outside the incubator 12. It could be mounted in any convenient manner such as by being fixed to the side of the respiratory gas source 16 as shown. A respiratory supply tube 202 connects the supply fitting of the humidifier, through a trap 204, to a supply fitting 206 of the incubator 12. An exhaust tube 208 interconnects the return fitting of the humidifier 200 and the return fitting 210 of the incubator. A second condensation trap 212 is connected in the return line.

Figure 12:
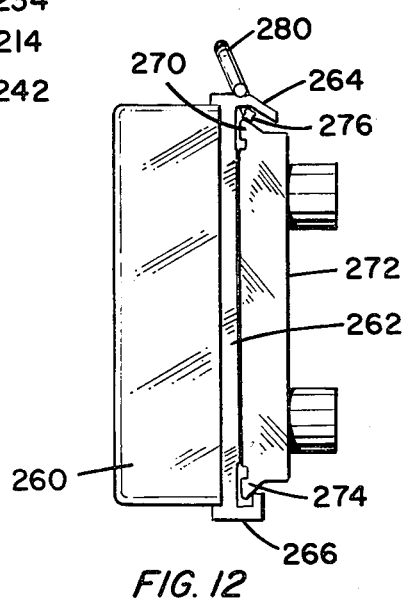
FIG. 12 is a view in end elevation of an alternative form of humidifier structure.

Except for differences in the elements by which the humidifier and heater are interconnected, as shown in FIG. 12, the unit 200 is like the humidifying structure 20. The supply and exhaust hoses are longer when the humidifying structure is mounted outside the infant enclosure, and they may be subjected to lower temperatures. Condensation of moisture inside the hoses is possible. Accordingly, each hose incorporates a means of some kind for collecting condensation. In preferred form that means is a condensation trap like traps 204 and 212.

Figure 10:
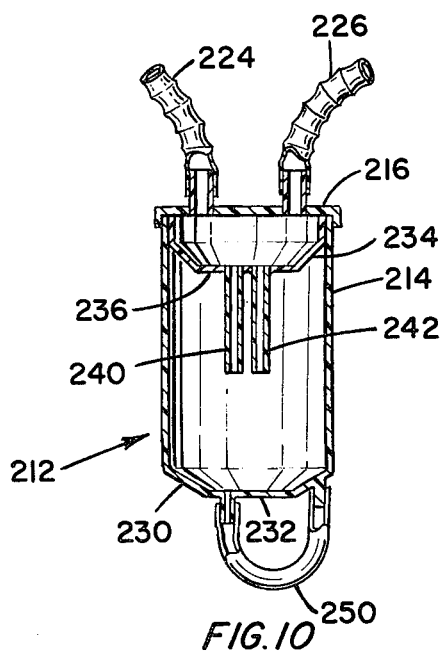
FIG. 10 is a cross-sectional view taken on line 10—10 of FIGS. 8 and 9.
Figure 11:
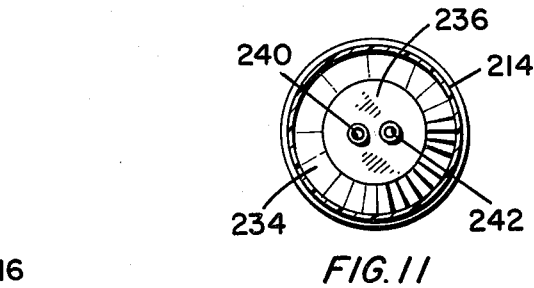
FIG. 11 is a cross-sectional view taken on line 11—11 of FIG. 7.

Trap 212 is shown in FIGS. 7 through 11. It comprises a generally cylindrical outer wall 214 one end of which is closed by a flat cover 216 from which two spaced nipples 220 and 222 extend upward, one to receive the inlet side 224 of a flow tube, and the other receive the outlet side 226 as shown in FIG. 10.

The lower end of the cylinder is closed by a truncated conical wall 230 and a flat bottom wall 232. The wall 232 extends over the small diameter end of the conical section. The other end of the section is bonded to the lower end of cylindrical wall 214.

The interior of the cylinder is divided into two chambers by an interior wall which includes a similar truncated wall section 234. The wider diameter rim of the section is bonded to the upper end of cylinder 214, and the lower diameter end of section 234 is closed by flat wall 236. This combination of conical section and flat bottom is an easily produced approximation of a continuously curved wall. The specific shape is less important than the fact that water flows easily over these two wall areas one to close the end of the cylinder and the other to form the dividing wall within the cylinder.

Communication between the two chambers is affored by two cylindrical tubes 240 and 242. They are spaced side by side at the lower surface of the flat wall. The axes of these tubes are parallel with that of the cylinder and the nipples 220 and 222 and the outlet tube 244 which extends below the lower wall 230 and opens to the lower chamber 238. A short length of flexible tubing 250 has one end assembled over the outlet tube 244. Its other end is assembled on a stub 252 which, being solid, seals the outlet tube.

The volume of the two chambers 236 and 238, the spacing and length of the water collection tubes 240 and 242, the direction in which fittings 220 and 222 extend, are all selected to insure that condensation in the respiratory supply and exhaust lines is removed and cannot return. The fittings 220 and 222 extend in like direction so that the flexible tubing sections 224 and 226 will arrive at and leave the trap in opposite directions. They form a V-shape, or are parallel, such that the trap is located at the apex of the V. The trap being heavier than the flexible tubing, extends down so that any moisture runs down the flexible tubing into the upper chamber of the trap and cannot move up the other flexible tube. The arrangement of inlets minimizes liquid "blow through."

Respiratory or exhalation gas in the tube varies in pressure. It is pulsed ad the pulses aid in moving any condensation over the surface of the inner bottom 236 and into one or both of the drain tubes 240 and 242. One will receive more than the other, and in view of surface tension, will be closed or partially closed. Pressure pulses will force the moisture down into the lower chamber while the other of tubes 240 and 242 permits air flow between chambers to relieve any slight pressure differential. The use of two tubes to connect the small flow chamber with the larger collection chamber results in substantially immediate removal of condensate from the flow chamber to the collection chamber.

The collection chamber must be drained before the water level there reaches the open ends of the drain tubes. The trap is drained by removing the end of the drain tube from the plug 252.

The passageway through the drain tube 244 is sufficiently small so that the rate of respiratory gas escape when the chamber is drained of water is low enough not to adversely affect the main flow of respiratory gas, but large enough to permit pressure sensors to detect the fault.

The volume of the portion of the lower chamber above the lower end of the drain tubes, and the volume at the side of the drain tubes in which water can collect, is less in any orientation of the trap than is the volume of the lower chamber below the drain tubes when the trap is vertical. That means that even if the trap is turned completely upside down, water cannot be returned to the gas flow chamber from the collection chamber. The two drain tubes are placed close together, far from the outer wall, to insure that feature.

The use of two collection tubes 240 and 242 is preferred when the system is subjected to pressure pulses. In applications wherein pressure is more uniform, the two parallel tubes may be replaced by a single, larger diameter tube, positioned centrally and extending to about the same level as do the tubes 240 and 242. Such a single tube will drain the flow cavity and equalize pressure between the two cavities and it will prevent drain back into the flow cavity in the event that the trap becomes inverted.

An alternative arrangement for clamping the heater to the back of the humidifier is shown in FIG. 12. As in the previously described construction the two units are assembled by inserting the evaporator unit lengthwise so that tracks on one unit fit within jaws on the other. In FIG. 12 the heater unit 260 includes a flat heat transfer plate 262. An upper jaw 264 extends across the length of the upper edge of the plate. A lower jaw 266 extends along the length of the lower edge. An upper foot or flange 270 extends across the upper rear edge of the evaporator 272. The outer forward edge of both of these flanges, 270 and 274 is tapered. The upper jaw 264 has a sloping surface facing the flange 270 and spaced from it. A rod 276 extends the length of the heater and evaporator units, and it is disposed in that space. The surface of the rod is serrated to simulate a toothed wheel, and it is provided with a handle 280 by which the rod 276 may be rotated a quarter turn. The space between the sloping surfaces of the foot 270 and the flange 264 is tapered to a lesser width in the direction away from the heater. Rotation of the handle causes the rod to be driven over the surface of foot 270 in the direction of lesser spacing. The result is that the evaporator foot 274 at the lower edge is driven down and toward the heater. At the upper edge the foot 270 is forced away from jaw 264 such that the back of the evaporator is forced against the heat transfer plate 262 into good thermal contact.

A pin is carried by the handle 280. The pin is disposed in a shallow detent when the handle is in the unlocked position shown. When the evaporator is to be locked to the heater the handle is rotated from the detent position in the clockwise direction.

Although we have shown and described certain specific embodiments of our invention, we are fully aware that many modifications thereof are possible. Our invention, therefore, is not to be restricted except insofar as is necessitated by the prior art.

We claim:

1. The method of heating and humidifying respiratory gas to be delivered to a patient at a delivery station from a gas source, which method comprises the steps of:
    forming a film of water on the surface of a body of heat conductive material;
    heating the outer surface of the film by applying heat to the body of heat conductive material;
    causing respiratory gas to flow over said outer surface of the film during transit from said source to the delivery station at a point proximate to said delivery station;
    said film of water being formed by permitting water to migrate, under the influence of gravity, from an upper region to a lower region of said surface of a body of heat conductive material; and
    further comprising the steps of removing unused and exhaled gas, and flowing said unused and exhaled gas over a lower region of said surface during removal whereby to remove any excess of water.

2. The invention defined in claim 1 which comprises the further step of varying the heat energy applied to said body of heat conductive material as a function of the temperature at said delivery station of the combination of newly supplied gas, unused gas, and exhaled gas.

3. In combination:
    humidifying means in the form of a heat conductive surface and means for forming a film of water on said surface by migration of water over said surface from one region to another, when supplied with water, and means for flowing respiratory gas over said surface for humidifying the respiratory gas;
    heating means in the form of a heater in thermal contact with said heat conductive surface for heating the water at the outer surface of said film and the respiratory gas flowing over said film;
    said conductive surface of said humidifying means being formed of a material whose appearance is altered when wet, and means in the form of a transparent cover for permitting viewing of said regions of said surface.

4. In combination:
    humidifying means in the form of a heat conductive surface and means for forming a film of water on said surface, when supplied with water, and means for flowing respiratory gas over said surface for humidifying the respiratory gas;
    heating means in the form of a heater in thermal contact with said heat conductive surface for heating the water at the outer surface of said film and the respiratory gas flowing over said film;
    said conductive surface of said humidifying means being formed of a material whose appearance is altered when wet, and means permitting viewing of regions of said surface which are wetted successively; and
    said means for flowing respiratory gas over the heat conductive surface comprising an element overlying said heat conductive surface and shaped to form a labyrinth passage having said heat conductive surface as one of its walls, said element being sufficiently transparent to permit visual observation of said heat conductive surface.

5. In combination:
    humidifying means in the form of a heat conductive surface and means for forming a film of water on said surface, when supplied with water, and means for flowing respiratory gas over said surface for humidifying the respiratory gas;
    heating means in the form of a heater in thermal contact with said heat conductive surface for heating the water at the outer surface of said film and the respiratory gas flowing over said film; and
    said heat conducting surface being one over which water will migrate as a consequence of gravitational force and which invention further comprises means for holding said heat conducting surface such that a first region of the surface lies above and second region of the surface; and
    means for applying water to said first region, said means for flowing respiratory gas comprising means for causing said gas to flow over said second region of the surface only after the gas has flowed over the first region of the surface and thereafter has been removed from said surface.

6. In combination:
humidifying means in the form of a heat conductive surface and means for forming a film of water on said surface, when supplied with water, and means for flowing respiratory gas over said surface for humidifying the respiratory gas; and
heating means in the form of a heater in thermal contact with said heat conductive surface for heating the water at the outer surface of said film and the respiratory gas flowing over said film;
said humidifying means comprising:
a heat conducting member having a substantially flat heat conducting surface over which water will migrate;
flow control means for permitting application of water to a first region of said heat conducting surface and for defining a flowpath for respiratory gas over a second region of said heat conductive surface, said flow control means comprising a structure having a planar surface overlying said heat conductive surface, said planar surface being recessed at the portions thereof that overlie said first and said second regions of the heat conductive surface.

7. The invention defined in claim 6 in which said heat conductive surface has a different appearance when wet than it has when dry and in which the flow control means is sufficiently transparent so that said second region of the heat conductive surface is visible through said flow control means.

8. Humidifying means comprising:
a heat conducting member having a substantially flat heat conducting surface over which water will migrate;
flow control means for permitting application of water to a first region of said heat conducting surface and for defining a flowpath for respiratory gas over a second region of said heat conductive surface, said flow control means comprising a structure having a planar surface overlying said heat conductive surface, said planar surface being recessed at the portions thereof that overlie said first and said second regions of the heat conductive surface.

9. The invention defined in claim 8 in which said heat conductive surface has a different appearance when wet than it has when dry and in which the flow control means is sufficiently transparent so that said second region of the heat conductive surface is visible through said flow control means.

10. A moisture trap in the form of a container having a gas flow cavity over a condensate collection cavity and a pair of drain passages interconnecting said chambers, the gas flow cavity being formed with gas flow inlet and outlet ports;
said trap comprising a pair of flow tube connectors communicating from the exterior of the trap to the gas flow cavity, said connectors being positioned such that tubes connected to them extend from the trap in directions that are substantially alike.

11. The trap defined in claim 10 which further comprises a drain tube extending from the collection cavity.

12. The invention defined in claim 11 which further comprises a tube plug carried by the trap and a length of tubing, the drain tube being coupled to one end of the length of tubing and the plug attached to and closing the other end.

13. In combination:
humidifying means in the form of a heat conductive surface and means for forming a film of water on said surface, when supplied with water, and means for flowing respiratory gas over said surface for humidifying the respiratory gas; and
heating means in the form of a heater in thermal contact with said heat conductive surface for heating the water at the outer surface of said film and the respiratory gas flowing over said film;
each of said heater and said humidifying means being structured to be separable from the other and which further comprises a pair of jaws on one and respectively associated flanges of a pair on the other for maintaining the heater and humidifying means in thermal contact.

14. The invention defined in claim 13 which further comprises means for forcing said heater and humidifying means into thermal contact by forcing separation of one of said flanges from its associated jaw such that the other flange is forced toward its associated jaw.

15. The invention defined in claim 13 in which said means for flowing gas over said surface comprises a flow tube in which a condensate trap is included, the condensate trap comprising a moisture trap in the form of a container having walls which define a gas flow cavity and a condensate collection cavity and a pair of drain passages interconnecting said cavities, said walls being formed with means in the form of a pair of ports in said wall communicating with said gas flow cavity for connecting said gas flow cavity in series with said flow tube.

16. The invention defined in claim 15 in which said condensate trap further comprises a drain tube extending from the collection cavity.

* * * * *